(12) United States Patent
Kim

(10) Patent No.: US 11,854,686 B2
(45) Date of Patent: Dec. 26, 2023

(54) DRUG-FREE THERAPEUTIC METHODS AND SYSTEMS FOR CHILDREN WITH AUTISM

(71) Applicant: Euy Chul Kim, Daejeon (KR)

(72) Inventor: Euy Chul Kim, Daejeon (KR)

(*) Notice: Subject to any disclaimer, the term of this patent is extended or adjusted under 35 U.S.C. 154(b) by 383 days.

(21) Appl. No.: 17/340,938

(22) Filed: Jun. 7, 2021

(65) Prior Publication Data

US 2022/0148705 A1    May 12, 2022

(30) Foreign Application Priority Data

Nov. 11, 2020    (KR) .................. 10-2020-0149910

(51) Int. Cl.
*G16H 20/70*    (2018.01)
*A61B 5/00*    (2006.01)
*A61B 5/16*    (2006.01)

(52) U.S. Cl.
CPC ............ *G16H 20/70* (2018.01); *A61B 5/168* (2013.01); *A61B 5/4842* (2013.01); *A61B 2503/06* (2013.01)

(58) Field of Classification Search
CPC ........ G16H 20/70; G16H 50/20; G16H 10/20; G16H 50/30; G16H 80/00; A61B 5/168; A61B 5/4842; A61B 2503/06; A61B 5/165; A61M 21/00
See application file for complete search history.

(56) References Cited

U.S. PATENT DOCUMENTS

2019/0043610 A1* 2/2019 Vaughan ............... G16H 10/60
2019/0355454 A1* 11/2019 Deshpande ........... G16H 40/67

* cited by examiner

*Primary Examiner* — Charles R Kasenge
(74) *Attorney, Agent, or Firm* — IPLA P.A.

(57) ABSTRACT

A therapeutic system for children's autism including a management server, a network, a client terminal and a database, wherein the management server includes a subject determination unit that determines whether or not the subject corresponds to the brain type to be treated through the client terminal; a mission presentation unit that presents a mission to a guardian through the client terminal if the subject corresponds to the brain type to be treated; an effect determination unit that determines whether or not there is a therapeutic effect through the treatment progress input through the client terminal after the guardian's mission is progressed; and a result output unit that outputs the determination result of the effect determination unit to the client terminal.

6 Claims, 1 Drawing Sheet

DRUG-FREE THERAPEUTIC METHODS AND SYSTEMS FOR CHILDREN WITH AUTISM

CROSS-REFERENCE

This application claims the benefit of Korean Patent Application No. 10-2020-0149910 filed 11 Nov. 2020, the entire contents of which are incorporated herein by reference.

BACKGROUND

The present invention relates to a neurological therapeutic method and system capable of treating or preventing children showing autism symptoms within a short time without the use of drugs.

This section provides background information related to the present disclosure which is not necessarily prior art.

Autism is a developmental disorder that exhibits delayed or abnormal functions in social skills, language, communication development, etc., and appears as a pattern of low interest in language expression-understanding, attachment to mothers, and play with people before the age of 3. This is a developmental disorder after the age of $3^{th}$ at is accompanied by a marked lack of interest in peers, stereotypy (repetitive behavior), severe withdrawal of play behavior, and decreased cognitive development, and is also known as an overall developmental disorder.

To date, there have been no clear cases of treatment for autism children, either drugs or non-drugs. According to the Harvard University autism research institute, 'the cause of the onset or therapeutic method has not been identified yet, but there are cases where it is treated by accident.' There are claims that it is treated with herbal medicine, but this does not guarantee a complete recovery. Global research on such autism seeks to find the cause from (1) the genetic aspect and (2) the neurological aspect, but the clear cause has not been clearly identified, so now only experimental treatments are repeated.

According to data from the National Statistical Office, as shown in Table 1, from 2001, for 18 years, the number of autisms in Korea has increased by about 11 times, and the real increase rate is 19 times taking into account the decline in the fertility rate. The increase was markedly different for each autism level, with the most severe level 1 autism increased 26 times, level 2 autism increased 17 times, and the mildest level 3 autism increased about 14 times over 18 years. As a result, it can be seen that the treatment of mild patients who have entered autism has not been performed at all, and that mild patients with level 3 have continued to regress to level 2 and level 1 without any countermeasures as they get older.

TABLE 1

| (Person) | 2001 | 2010 | 2018 |
|---|---|---|---|
| Level 1 | 715 | 7,517 | 10,472 |
| Level 2 | 1,265 | 4,945 | 12,158 |
| Level 3 | 536 | 2,426 | 4,073 |
| Total | 2,516 | 14,888 | 26,703 |

In addition, as shown in Table 2, it can be seen that people with autism, who were distributed mainly at a young age, are distributed evenly to the age of 30s as the years go by. As a result, in about 20 years, people with autism will be distributed across all ages in Korea, and it is predictable that the absolute number will rise to 0.1% from the current 0.05% compared to the entire population.

TABLE 2

| (Person) | 2007 | 2010 | 2019 |
|---|---|---|---|
| Age of 9↓ | 4,181 | 3,262 | 6,962 |
| Age of 10s | 6,345 | 8,656 | 9,526 |
| Age of 20s | 1,127 | 2,657 | 9,440 |
| Age of 30s | 136 | 245 | 2,455 |
| Total | 11,789 | 14,820 | 28,383 |

SUMMARY OF THE DISCLOSURE

An object of the present invention is to provide a therapeutic method and system capable of treating autism children under the age of 12 without the use of drugs.

However, the objects of the present invention are not limited to the above-mentioned objects, and other objects not mentioned will be clearly understood by those skilled in the art from the following description.

The present invention provides a therapeutic system for children's autism comprising a management server, a network, a client terminal and a database, wherein the management server comprises a subject determination unit that determines whether or not the subject corresponds to the brain type to be treated through the client terminal; a mission presentation unit that presents a mission to a guardian through the client terminal if the subject corresponds to the brain type to be treated; an effect determination unit that determines whether or not there is a therapeutic effect through the treatment progress input through the client terminal after the guardian's mission is progressed; and a result output unit that outputs the determination result of the effect determination unit to the client terminal.

Further, the present invention is characterized in that the client terminal is a terminal that guardian accesses the management server through the network, inputs information for determining whether or not it corresponds to the brain type to be treated, and information on the treatment progress by step, and then the result of determination on the therapeutic effect is output through a screen or a connected printer after performing the presented mission.

Further, the present invention is characterized in that the management server presents the guardian mission comprises Mission group 1 for blocking neural network damage factors through the mission presentation unit; Mission group 2 for removing the neural network damage factors; Mission group 3 for recovering and activating the neural network; Mission group 4 for promoting neurotransmitter production; and Mission group 5 for intensive treatment of autism.

Further, the present invention is characterized in that the Mission group 1 includes 4 or more detailed missions selected from the mission group consisting of pretending not to be unaware of the wrongdoing, not speaking with instruction and command, not forcing to follow the rules, not feeding harmful food, not disgracing in public place, not forcing to bow down, not fighting other guardians, and not apologizing for wrongdoing.

Further, the present invention is characterized in that the Mission group 2 includes 4 or more detailed missions selected from the mission group consisting of not strongly restraining behavior, improving the residential environment, giving way to competing, dressing airy clothes and shoes, not forcing to study math, not burdening reading and writing, not forcing to organize and disciplining simply.

Further, the present invention is characterized in that the Mission group 3 includes 4 or more detailed missions selected from the mission group consisting of prohibiting reading and read instead, not being sarcastic in case of interpersonal conflict, getting the attention of others in one body, not feeling bothered, exaggerating or conversely praising, actively helping role-play, spending more time outside, and responding to the subject's lies or fictional expressions caused by imagination.

Further, the present invention is characterized in that the Mission group 4 includes 4 or more detailed missions selected from the mission group consisting of doing a lot of outdoor activities in autumn and winter, not looking down, making the subject laugh out loud and often, wake up in the morning through skinship, positively accepting unreasonable demands, avoiding the burden of school homework, praising in crowded place, and praising wrong doings in reverse.

Further, the present invention is characterized in that the Mission group 5 includes 4 or more detailed missions selected from the mission group consisting of using the titles of prince and princess, teaching swimming, provide supplementary explanations for immediate denial, speaking in child-centered language, taking on the supervisory role, starting conversations with specific issues, actively responding to active contact, and going on a trip.

By using the therapeutic method and system according to the present invention, autism children under the age of 12 can be treated within 5 to 7 months without the use of drugs. If autism is neglected, it regresses to a disorder, so the occurrence of a level 3 disorder can be prevented by the therapeutic method and system according to the present invention.

More specifically, the therapeutic system of the present invention recovers damaged brain and artificially produces neurotransmitter, which is advantageous for autism treatment, by changing environmental factors of autism children so that autism treatment is possible. In addition, the longer the exposure is to such an environment, the greater the effect, so by intervening the caregiver as a therapist, children's autism can be treated within 5 to 7 months without the use of drugs.

DETAILED DESCRIPTION OF THE INVENTION

Figure 1:
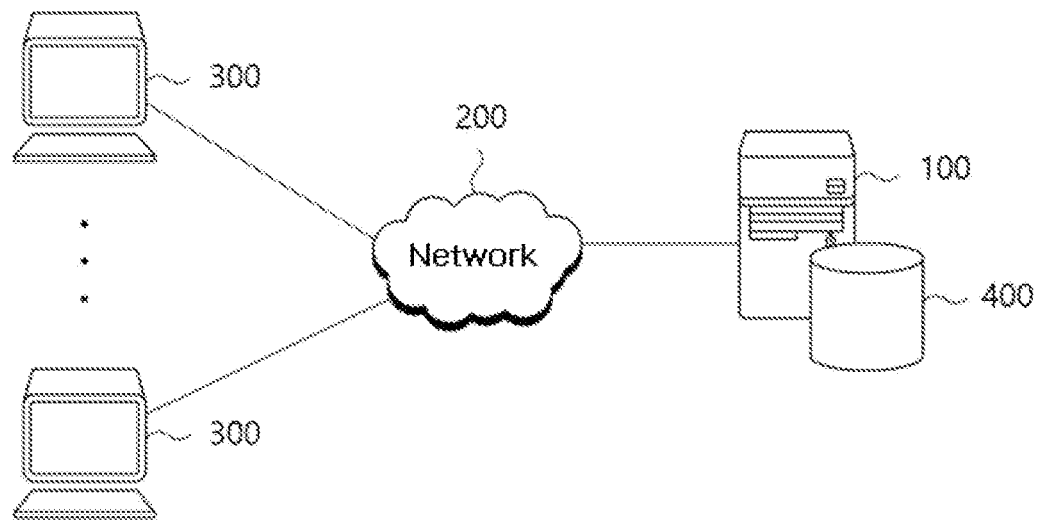
FIG. 1 shows a schematic diagram of a children's autism therapeutic system to which a therapeutic method according to one embodiment of the present invention is applied.

Unless otherwise defined, all terms including technical and scientific terms used herein have the same meaning as commonly understood by those of ordinary skill in the art. In addition, throughout the specification and claims, unless otherwise stated, the term "comprise, comprises, comprising" means to include the recited object, step or group of objects or group of steps, and is not used to exclude any other object, step or group of objects or group of steps.

Before describing the present invention in detail below, it should be understood that the terms used herein are for describing specific embodiments and are not intended to limit the scope of the present invention, which is limited only by the scope of the appended claims.

On the other hand, various embodiments of the present invention may be combined with any other embodiments unless clearly indicated to the contrary. Any feature indicated to be particularly desirable or advantageous may be combined with any other feature and features indicated to be desirable or advantageous. Hereinafter, embodiments of the present invention and effects thereof will be described with reference to the accompanying drawings.

The drug-free therapeutic method for children showing autism symptoms according to the present invention will be described in detail with reference to the accompanying drawings.

The human brain is classified into 5 types as follows according to its characteristics, and each type has characteristics that are both strong and vulnerable to certain diseases.

Type 1: Extreme Right Hemisphere Dominant (ERHD)
Type 2: Right Hemisphere Dominant (RHD)
Type 3: Right-Left Balanced (BH)
Type 4: Left Hemisphere Dominant (LHD)
Type 5: Extra Left Hemisphere Dominant (ELHD)

How different brain types have different characteristics, and 20 representatively different characteristics based on children up to 12 years old are shown in Table 3 below.

TABLE 3

|  | Type 1 | Type 2 | Type 3 | Type 4 | Type 5 |
| --- | --- | --- | --- | --- | --- |
| Creativity + Logicality | Extremely Creative | Very Creative | Creative + Logical | Very Logical | Completely Logical |
| Activity | Extremely Active | Very Active | Occasionally Active | Slightly Active | Inactive |
| Personality | Very Quick Tempered | Impatient | Moderate | Relaxed | Very Relaxed |
| Emotional Expression | Extremely Expressive | Very Expressive | Moderately Expressive | Seldom Expressive | Non-expressive |
| Sociality | Nonsocial (Extremely poor) | Highly Developed | Embracing | Relates Selectively | Nonsocial (Extremely poor) |
| Self-control | None | Occasionally | Usually Good but sometimes explode | Excellent | Extremely Proficient |
| Reaction Velocity | Extremely Quick | Very quick | Moderate | Slow | Extremely Slow |
| Understanding | Extremely Quick | Very quick | Moderate | Slow | Very Slow |

TABLE 3-continued

|  | Type 1 | Type 2 | Type 3 | Type 4 | Type 5 |
| --- | --- | --- | --- | --- | --- |
| Sentence Recollection | Very Weak Dyslexia before Age 10 | Weak | Moderate | Good | Excellent |
| Image Information Recollection | Excellent | Very good | Moderate | Bad | Very bad |
| Thoughtfulness | Thoughtless | Slightly Thoughtful | Very Excellent | Selfish | Very selfish |
| Rule, Promise | Does Not Follow | Follows on occasion | Flexible | Follow well | Follows All Rules Completely |
| Punishment | Severe Punishment Can Cause Brain Trauma | Effective | Accumulation of Disbelief | Endeavor to Avoid Punishment | Does not Need to Be Punished |
| Ability to follow directions | Disobedient to Persuasion and Direction | Rarely Obedient | If directions sounds reasonable, follows well | Obedient well | Very Obedient |
| Fine Motor Skill | Extremely Weak | Strong | Strong | Strong | Strong |
| Eye Contact | Good, Powerful | Good | Medium (Half and Half) | Not Good | Seldom |
| Violence | Extremely High | Very High | Only for Public Interest | Only for Self-protection | Completely nonviolent |
| Obsession | Strong | Weak | Rarely | Weak | Strong |
| Fear | Fear at Slight Provocation | Easily Frightened | Medium | Seldom Frightened | Not Frightened |
| Aptitude Field | Art, Linguistic Ability, IT, Politics, Law | Art, Acting, Visual Art, Sports | Management, Legal Circles, Dental, Medical, Teaching, Marketing | Dental, Medical, Teaching, Architecture, Natural Science | Basic - Pure Science, Research, Writing |
| Distribution in the ROK | 4.1% | 46.4% | 23.5% | 25.9% | 0.1% |

The human brain controls humans. What makes the brain brain-like is the synapse, which is constantly recreated. The brain develops by appropriate stimulation, but is damaged by excess, long-term stimulation. Environmental factors have a significant influence on brain development and function.

On the other hand, there are about 50 neurotransmitters known to be produced by the brain, and although the amount of each is extremely small, it has an absolute influence on the functioning of the human body. For example, a lack of serotonin leads to aggressive tendency, and too much serotonin leads to obsessions and makes you obsess over too much detail.

The present inventors have found that it is possible to produce 'specific neurotransmitter' by external efforts, and this helps to treat autism. Through this, by changing the environmental factors of autism children under 12 years of age, it artificially recovers the damaged brain and artificially produces neurotransmitter, which is advantageous for autism treatment, thereby providing an effect that can treat autism children.

Brain types showing autism symptoms are limited to type 1 and type 5 (ERHD, ELHD), and especially autism symptoms appear when a person corresponding to type 1 suffers serious damage to the cranial nerves. In the case of type 5 (ELHD), in Korea, the corresponding person is extremely rare (less than 0.1%), and as shown in Table 4 below, the characteristics of the type correspond to autism symptoms and are not symptoms due to brain damage. Therefore, the autism treatment in the present invention is aimed at treating type 1 (ERHD) brain damage.

TABLE 4

| Characteristics of Autism |
| --- |
| 1. Impairments in social interaction |
| 2. Impairments in communication (=Speech Delay) |
| 3. Repetitive (=Stereotyped) behavior |
| 4. Less active to social stimuli |
| 5. Expressionless even in funny things |
| 6. Less responsive to their own name |
| 7. Less eye contact |
| 8. Lacking the ability to point at things |
| 9. Screaming badly if it is out of his control |
| 10. Cannot play with many people, and do not want to take group photos |
| 11. Cannot imitate & respond to emotions |
| 12. Communicates nonverbally |
| 13. Prone to intense & frequent loneliness |
| 14. Difficulty in making & maintaining friendships |
| 15. Aggressive |
| 16. Tendency to destroy property |
| 17. Exceptionally sensitive to mechanical sounds (vacuum cleaner) |
| 18. Cannot associate word combinations |

TABLE 4-continued

19. Gestures that are less integrated with words
20. Imitate the opponent's ending (Echolalia)
21. Play imaginary games like real (Call like real on a toy phone, feeding dolls, etc.)
22. Has difficulty developing symbols into language.
23. Tendency towards compulsive behaviors
24. resisting to change and being settled in the same habits
25. Restricted interests
26. Self-harm
27. Sensory abnormalities
28. Toe walking
29. Atypical eating
30. Clambering onto bookshelf and other furniture Characteristics of Normal
Type 1 (ERHD)

1. Nonsocial
2. Articulate oral expression, Good communication skills
3. Broad spectrum of activity, Energetic
4. Very creative, Effort for become a unique individual
5. Auditory senses are outstanding
6. Emotional expression is good
7. Staring intensely like eyes are shooting a laser
8. Deficits in motor coordination
9. Lack of self-control
10. Characteristic of extremely quick reactive velocity
11. Characteristic of superb image information recollection
12. Does not follow the rule, promise
13. Tendency towards excessive violence
14. Has extremely strong obsessive behaviors
15. Fear at the slightest provocation Characteristics of Normal
Type 5 (ELHD)

1. Nonsocial
2. Extremely slow oral expression; grammatically correct
3. Small range of activity, Inactive
4. Lack of creativity; Seeks logic
5. Superb concentration, If they concentrate extremely, they cannot listen other things.
6. Non facial emotional expression
7. Seldom shows eye contact.
8. Inactive however well-developed in fine motor skills
9. Strong self-control, Very passive attitude
10. Extremely slow response characteristic (Sometimes after 1-2 weeks)
11. Superb sentence recollection
12. Characteristic of complete rule and promise compliance.
13. Completely nonviolent, inherence
14. Very competitive, Obsessive
15. Not frightened (=10. Extremely slow response)

The present invention has industrial applicability by developing a method (therapeutic method) to remove the cause (offset) based on the principle that such autism caused by brain damage of ERHD is cured if the cause is removed or canceled.

The principles of treatment according to the present invention are summarized as follows.

1. Cranial Nerve System Therapy

The cause of autism is due to damage to the cranial nerve system such as synapse, so autism begins to be treated by correcting the cranial nerve system, such as actively creating a new synapse. In addition, autism is treated more reliably by generating beneficial neurotransmitter.

2. Preventive Therapy

Children's autism is caused by: ① Enforcement of rules and scolding while living in groups in kindergartens, schools, etc ② Parents' excessive desire to teach social norms ③ Shock, ridicule, bullying, etc. from playing with their peers.

Therefore, autism treatment should be done at the same time as a) treating the brain damage that has already been inflicted and b) preventing further damage in the future.

3. ERHD Autism Targeted Therapy

Autism symptoms appear when a person corresponding to type 1 suffers serious damage to the cranial nerves. In the case of type 5 (ELHD), in Korea, the corresponding person is extremely rare (less than 0.1%), and the characteristics of the type correspond to autism symptoms and are not symptoms due to brain damage. Therefore, the autism treatment in the present invention is aimed at treating type 1 (ERHD) brain damage.

4. 24-Hour Therapy

The first factor that damages the cranial nerves is a bad environment. The backtracking-offset of this environment is the basis of the therapy, and this invention informs the guardian of the treatment once a week, and allows them to practice according to the mission for one week. As a result, since it is exposed to the therapeutic system 24 hours a day, 168 hours a week, the therapeutic effect is fast. The mission is the conversion of the therapeutic method of the damaged cranial nerve into a "guardian version", so any non-disabled guardian can practice it as much as possible.

5. Treatment Under Siege

Treatment of damaged cranial nerves should not be dependent on only counseling. The 5 factors that recover the cranial nerve tissue include: ① Guidelines in the house, ② Teaching methods, ③ Food, ④ Clothes and living environment, ⑤ Art and physical education. If any of the above 5 factors are lax, the recovery of the damaged cranial nerve network, that is, autism treatment slows or stalls in.

FIG. 1 shows a schematic diagram of a children's autism therapeutic system to which a therapeutic method according to a preferred embodiment of the present invention is applied. As shown in FIG. 1, the therapeutic system of the present invention consists of a management server 100, a network 200, a client terminal 300, and a database 400. The present invention is to provide a system that enables treatment by providing the above therapeutic method as a mission that can be executed by a guardian in order to besiegingly apply the method to autism children for 24 hours.

Figure 2:
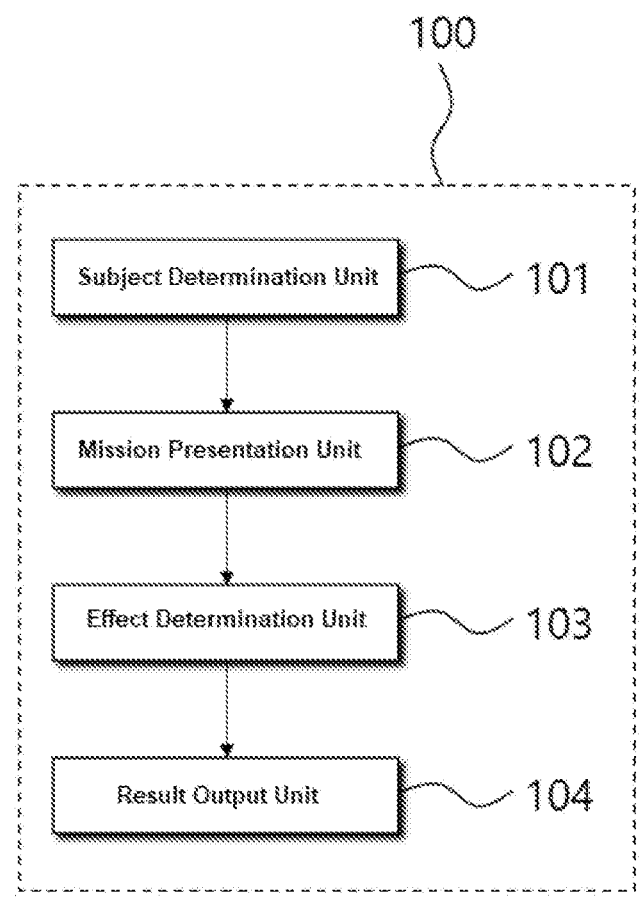
FIG. 2 shows a block diagram of a management server according to one embodiment of the present invention.

The management server 100 is a server that manages the entire treatment process, and as shown in FIG. 2, comprises a subject determination unit 101 that determines which brain type the subject corresponds to through the client terminal 300; a mission presentation unit 102 that presents a detailed mission by step to a guardian through the client terminal 300 if the subject corresponds to the brain type to be treated; an effect determination unit 103 that determines whether or not there is a therapeutic effect through the treatment progress input through the client terminal 300 after the detailed mission by step is progressed; and a result output unit 104 that outputs the determination result of the effect determination unit 103 to the client terminal 300.

The client terminal 300 is a terminal that guardian accesses the management server 100 through the network 200, inputs information for determining whether or not it corresponds to the brain type to be treated, and information on the treatment progress by step, and then the result of determination on the therapeutic effect is output through a screen or a connected printer after performing the presented detailed mission. This client terminal 300 may use any one of a desktop computer, or a mobile terminal such as a tablet, a smart pad, and a smart phone.

Further, the database 400 is a data storage device that stores the information entered by a guardian and stores information related to the therapeutic method. More specifically, a list of characteristics to determine whether or not it corresponds to the brain type to be treated, detailed missions for each mission group, and a list of expected treatment progress by mission or time to determine whether or not there is a therapeutic effect are stored.

Hereinafter, a method for treating autism of children using the system according to the present invention will be described in detail.

First, a guardian accesses the management server 100 through the client terminal 300 and inputs information on the subject to be treated (children). For example, the subject determination unit 101 can determine whether or not it corresponds to the brain type to be treated in such a way that, after inputting information including gender and age as information on the subject to be treated, a list of characteristics corresponding to each brain type is presented and checked.

When it is determined that it corresponds to the brain type to be treated, ERHD (type 1), and the guardian requests treatment, first, the management server 100 presents the guardian mission comprises Mission group 1 for blocking neural network damage factors to the client terminal 300; Mission group 2 for removing the neural network damage factors; Mission group 3 for recovering and activating the neural network; Mission group 4 for promoting neurotransmitter production; and Mission group 5 for intensive treatment of autism.

The Mission group 1 for blocking neural network damage factors, and includes 4 or more detailed missions selected from the mission group consisting of pretending not to be unaware of the wrongdoing (1-1-1), not speaking with instruction and command (1-2-2), not forcing to follow the rules (2-1-3), not feeding harmful food (2-1-4), not disgracing in public place (3-1-5), not forcing to bow down (3-2-6), not fighting other guardians (4-1-7), and not apologizing for wrongdoing (4-2-8).

When the detailed missions are presented sequentially in the Mission group 1, in the $1^{st}$ round, even if the subject to be treated is wrong, speak with good words and cover for the subject, and reassure that the intentional mistake is okay (1-1-1), and do not speak with instructions and command because autism children never obey orders and the symptoms of autism will intensify if they are ordered more (1-2-2). In the $2^{nd}$ ground, observance of rules is not enforced because rules, regulations and appointments are a factor of cranial nerve atrophy for the subject to be treated and when atrophy occurs, autism symptoms begin to appear (2-1-3), and provide a separate beneficial diet to avoid feeding harmful foods (2-1-4). In the $3^{rd}$ ground, refrain from embarrassing in a public place is a direct cause of autism as the subject to be treated is burned with vengeance and anger rises (3-1-5), and do not force a bowed greeting because it is a decisive behavior reducing self-esteem, leading to brain function decline and suppressing neurotransmitter (3-2-6). In $4^{th}$ ground, do not fight where the children can see because in early childhood, parents are the best guardians and refugee, and when the parents are collapsed, the children are shocked (4-1-7), and if something is wrong, replace it with shaking hands or hugging and do not apologize because for ERHD, 'apology' is a factor that hinders brain function (4-2-8).

The Mission group 2 is for removing the neural network damage factors, and includes 4 or more detailed missions selected from the mission group consisting of not strongly restraining behavior (5-1-9), improving the residential environment (5-2-10), giving way to competing (6-1-11), dressing clothes and shoes with airy things (6-2-12), not forcing to study math (7-1-13), not burdening reading and writing (7-2-14), not forcing to organize (8-1-15), and disciplining simply (8-2-16).

When the detailed missions are presented sequentially in the Mission group 2, in the $5^{th}$ ground, do not 'absolutely' use language such as no, do not or stop about the behavior of the subject to be treated (5-1-9), and improve the living environment because high temperature and high humidity or enclosed places increase irritation, especially by causing atopy or rhinitis, and they try to escape alone to a cool place (5-2-10), in $6^{th}$ ground, it is better to give way to competing, but to lose it technically (6-1-11), and make sure clothes and shoes are well ventilated so that heat does not accumulate on their body and their body functions are not reduced (6-2-12). In $7^{th}$ ground, do not force to study math because the brain related to math of the subject to be treated is incomplete (7-1-13), and because children are weak in their small muscles and vulnerable to writing, and do not understand the meaning of letters but understand them through pictures, if forced to read and write, there is a concern that dyslexia may increase, so do not force it (7-2-14). In $8^{th}$ ground, do not force to organize because a neatly organized place is one of the factors slowing down the synapse function (8-2-16), and discipline simply and gently because if discipline is lengthy, it only causes anger and if speak with a serious face, they accept as a comment (8-2-16).

The Mission group 3 is for restoring and activating the neural network, and includes 4 or more detailed missions selected from the mission group consisting of prohibiting reading and read instead (9-1-17), not being sarcastic in case of interpersonal conflict (9-2-18), getting the attention of others in one body (10-1-19), not feeling bothered (10-2-20), exaggerating or conversely praising (11-1-21), actively helping role-play (11-2-22), spending more time outside (12-1-23), and responding to the subject's lies or fictional expressions caused by imagination (12-2-24).

When the detailed missions are presented sequentially in the Mission group 3, in the $9^{th}$ ground, prohibit reading and read instead as much as possible because most of the subjects to be treated have dyslexia and therefore the burden of reading leads to irritation and anger (9-1-17), and do not be sarcastic because in the case of interpersonal conflict, reaction such as "I told you not to play with him" immediately make them anger and increase autism tendency (9-2-18). In $10^{th}$ ground, since severe alienation can also be a direct cause of autism, brain function is activated by increasing presence by getting the attention of others in one body (10-1-19), and if neglected, atrophic brain damage will intensify, and if self-esteem is lost, neurotransmitter production will also stop, so not feeling bothered (10-2-20). In $11^{th}$ ground, feeling a thirst for praise is not enough to recover brain function, so exaggerating or conversely praising (11-1-21), and role-play is the realization of imagination and the driving force of reform as a test site for how to tolerate, so if children are playing role play alone, actively helping (11-2-22). In $12^{th}$ ground, in narrow spaces such as small rooms, indoors and cars, brain function is slowed and neurotransmitter production is distorted, so spending more time outside (12-1-23), and when a fictional expression by lies or imagination is transferred together and received as a scene in a fairy tale, the recovery of the damaged brain function is very fast (12-2-24).

The Mission group 4 is for promoting neurotransmitter production, and includes 4 or more detailed missions selected from the mission group consisting of doing a lot of outdoor activities in autumn and winter (13-1-25), not looking down (13-2-26), making the subject laugh out loud and often (14-1-27), wake up in the morning through skinship (14-2-28), positively accepting unreasonable demands (15-1-29), avoiding the burden of school homework (15-2-30), praising in crowded place (16-1-31), and praising wrong doings in reverse (16-2-31).

When the detailed missions are presented sequentially in the Mission group 4, in the 13$^{th}$ ground, in summer, exhaustion of physical strength is high, so do a lot of outdoor activities in winter to improve physical strength (13-2-15), and beneficial neurotransmitters are produced only when being treated as a mental and physical partner and feeling the position of "A", but anger explodes when feeling to be treated contemptuously, so not looking down (13-2-26). In 14$^{th}$ ground, it is dangerous to spend a lot of time alone quietly, so use various means to make laugh out loud, openly and often (14-1-27), and wake up naturally in the morning through special skinship (14-2-28). In 15$^{th}$ ground, unreasonable demand means a state of brain damage, and refusal in principle increases brain damage, so positively accept unreasonable demand (15-1-29), and the task of learning itself is a great stress, and reviewing at home makes anger at the peak, so make sure there is no burden for school homework and stop learning until recovered completely (15-2-30). In 16$^{th}$ ground, inspire heroism by complimenting in many places (16-1-31), and pointing out a mistake leads to a sudden increase in brain damage, so compliment for doing something wrong and praise doing well (16-2-32).

The Mission group 5 is for intensive treatment of autism disorder, and includes 4 or more detailed missions selected from the mission group consisting of using the titles of prince and princess (17-1-33), teaching swimming (17-2-34), providing supplementary explanations for immediate denial (18-1-35), speaking in child-centered language (18-2-36), taking on the supervisory role (19-1-37), starting conversations with specific issues (19-2-38), actively responding to active contact (20-1-39), and going on a trip (20-2-40).

When the detailed missions are presented sequentially in the Mission group 5, in the 17$^{th}$ ground, repair damage cleanly by confirming that the children are a superior existence by using the title of Prince and Princess (17-1-33), and create an opportunity to learn to swim to boost neurotransmitter production (17-2-34). In 18$^{th}$ ground, immediate denial is due to lack of information, and 'I hate it!' means 'Please explain well', so provide supplementary explanations kindly (18-1-35), and for example, children refuse when saying 'it's time to go somewhere', so the children are said to be a main character, not a subordinate, by saying, 'Someone is waiting for you somewhere' (18-2-36). In 19$^{th}$ ground, desiring a supervisory role is a phenomenon seen when brain function is normalized, and the role of commander promotes neurotransmitter generation, so if they want the role of director, leave it to them (19-1-37), and for example, it is difficult to answer to 'What did you do today?', but it is easy to answer to such as 'Did you enjoy building blocks today?', so the conversation should be made on a specific issue (19-2-38). In 20$^{th}$ ground, respond positively to active skinship such as expression of affection and cute words or actions of the subject to be treated (20-1-39), and even after treatment is complete, make sure that their talents and stabilization are expressed through external activities, such as travel (20-2-40).

The interval for presenting the missions may be determined according to the target disorder and the choice of the guardian. For example, the mission presentation unit 102 may present a mission group at intervals of one month, and may present detailed missions included in each mission group at a time, or divide the detailed missions by week and present them over 4 to 5 times.

At this time, Mission group 1 to Mission group 5 may be provided sequentially, but is not limited thereto. First, Mission group 1 to Mission group 4 may be provided in any order, and then Mission group 5 may be provided, or first, Mission group 1 and Mission group 2 may be provided in any order, Mission group 3 and Mission group 4 may be provided in any order, and finally Mission group 5 may be provided.

The management server 100 can output to the client terminal 300 to input the treatment progress after performing the missions. The guardian inputs the progress (change) of the subject to be treated through the client terminal 300, and determines whether or not there is a therapeutic effect through information on the change that appears when there is a therapeutic effect stored in the Database 400. For example, the effect determination unit 103 provides a list of the expected treatment progress for each mission or time stored in the Database 400, and allows a guardian to check whether or not there is a therapeutic effect.

The management server 100 determines whether or not there is a therapeutic effect step by step, and if there is a therapeutic effect, it provides the next step mission. In addition, if the subject is cured during the mission, the mission at the later step can be omitted. If there is not therapeutic effect, the mission of a specific step is repeatedly presented.

The therapeutic effect varies according to the subject to be treated, but in general, after Mission group 3 is performed, there is a noticeable improvement. Subsequently, when Mission group 4 and Mission group 5 are repeatedly performed, incidentally, the therapeutic effects for Attention deficit hyperactivity disorder (ADHD), Tic, speech delay and intellectual delay can also be obtained.

The experimental results of treating a boy in the third grade of elementary school who was diagnosed with level 2 autism in a university hospital using the therapeutic system of the present invention are described below.

(1) Symptoms before the start of treatment of the subject to be treated

No friends to play with. (Sociality x)

Avoid verbalizing his thoughts. (Impairments in communication)

Stereotyped behaviors: Repeated clapping, hitting the corners with a measuring stick, spinning around the table, chewing and spitting gum every 1 to 2 minutes Don't smile broadly at good things.

There is no response to the name calling twice out of three.

Play well alone for a long time.

Obsessed with things and aggressive.

Atypical eating.

Persistent demands for a puppy, chameleon, cat and expensive IT products.

Don't want to go to the playground, academy or school.

Sit alone on the bench across the playground in school.

Avoid eye contact with parents or teachers.

There is hem and twitching lips as tic symptoms.

Talking in a loud voice into a toy phone, like a real life.

Talk to unfamiliar local adults first, and then try to have a conversation.

(2) Changes after performing Mission group 1 and Mission group 2 (after 2 months)

In 6 weeks, the atypical eating disappears, and the stool turns into a glowing banana shape.

Facial expressions brightened, and smiles became frequent.

Hem as a tic symptom, has clearly disappeared.

Began active contact with guardians (parents). (=Hitting mom, throwing light objects at dad, etc.)

A habit of hitting the corners with a measuring stick and a habit of spitting immediately after chewing gum have disappeared.

Aggressive behavior has been significantly reduced. (After 8 weeks)

(3) Changes after performing Mission group 3 (after 3 months)

Do not avoid eye contact with parents (from week 8 to 9).

Respond twice to the name calling three times.

There seems to be no request to buy a puppy, chameleon. IT product demand is continuing. There is a tendency to look for products with special functions.

Repeated clapping and spinning around the table among the stereotyped behaviors disappeared. Often observed doing something in front of a computer.

First time attending the institute workshop→Didn't have much conversation with peers→At a gathering attended by both parents (approximately 40 people)→Talking about two to three things his parents have done wrong to the subject←All of the parents who attended were surprised.

Twitching lips as tic symptoms disappeared. The habit of overeating also quietly disappeared. (After 10 to 12 weeks)

(4) Changes after performing Mission group 4 (after 4 months)

Response to the name calling every time. Same as normal children. Became neat.

Going to the playground, but still forced to go to school and return in 1 to 2 hours.

When he goes to school, he rarely sit alone across the playground, and sometimes make eye contact with the teacher. The feeling of intentionally avoiding disappeared.

Talking on a toy phone has been completely eliminated. It's so ridiculous that a boy in the third grade of elementary school played this kind of game.

Having a friend who swings at the playground together. Sometimes riding a bicycle and running neck and neck.

Playing with his three years younger sister. Before treatment, he only harassed his sister all the time.

Sometimes sharing his stuff to a friend who rides on a swing.

(5) Changes after performing Mission group 5 (after 5 months)

Talking a lot. Using funny stories and humor.

Said he made one best friend at school. Often hanging out with two or three people at the local playground and riding a bicycle. At home, playing with his younger sister and never been found to play alone.

Tending to go to school well and frolicking with children in a classroom and corridors during breaks.

Naturally making eye contact with parents, teachers and anyone else.

Saying hello to the local adults, but not feeling like intentionally taking to them. Natural interpersonal relationships.

After 18 to 19 weeks, autism treatment was completed without any medication.

Incidentally, ADHD, tics, speech delay and intellectual delay were also completely recovered.

The features, structures, effects, etc. exemplified in each of the above-described embodiments may be combined or modified for other embodiments by those skilled in the art. Therefore, contents related to these combinations and modifications should be construed as being included in the scope of the present invention.

What is claimed is:

1. A therapeutic system for children's autism comprising a management server, a network, a client terminal and a database, wherein the management server comprises a subject determination unit that determines whether or not the subject corresponds to the brain type to be treated through the client terminal; a mission presentation unit that presents a mission to a guardian through the client terminal if the subject corresponds to the brain type to be treated; an effect determination unit that determines whether or not there is a therapeutic effect through the treatment progress input through the client terminal after the guardian's mission is progressed; and a result output unit that outputs the determination result of the effect determination unit to the client terminal, wherein the management server presents the guardian mission comprises Mission group 1 for blocking neural network damage factors through the mission presentation unit; Mission group 2 for removing the neural network damage factors; Mission group 3 for recovering and activating the neural network; Mission group 4 for promoting neurotransmitter production; and Mission group 5 for intensive treatment of autism, and wherein the Mission group 1 includes 4 or more detailed missions selected from the mission group consisting of pretending not to be unaware of the wrongdoing, not speaking with instruction and command, not forcing to follow the rules, not feeding harmful food, not disgracing in public place, not forcing to bow down, not fighting other guardians, and not apologizing for wrongdoing.

2. The therapeutic system for children's autism of claim 1, wherein the client terminal is a terminal that guardian accesses the management server through the network, inputs information for determining whether or not it corresponds to the brain type to be treated, and information on the treatment progress by step, and then the result of determination on the therapeutic effect is output through a screen or a connected printer after performing the presented mission.

3. The therapeutic system for children's autism of claim 1, wherein the Mission group 2 includes 4 or more detailed missions selected from the mission group consisting of not strongly restraining behavior, improving the residential environment, giving way to competing, dressing airy clothes and shoes, not forcing to study math, not burdening reading and writing, not forcing to organize, and disciplining simply.

4. The therapeutic system for children's autism of claim 1, wherein the Mission group 3 includes 4 or more detailed missions selected from the mission group consisting of prohibiting reading and read instead, not being sarcastic in case of interpersonal conflict, getting the attention of others in one body, not feeling bothered, exaggerating or conversely praising, actively helping role-play, spending more time outside, and responding to the subject's lies or fictional expressions caused by imagination.

5. The therapeutic system for children's autism of claim 1, wherein the Mission group 4 includes 4 or more detailed missions selected from the mission group consisting of doing a lot of outdoor activities in autumn and winter, not looking down, making the subject laugh out loud and often, wake up in the morning through skinship, positively accepting unreasonable demands, avoiding the burden of school homework, praising in crowded place, and praising wrong doings in reverse.

6. The therapeutic system for children's autism of claim 1, wherein the Mission group 5 includes 4 or more detailed missions selected from the mission group consisting of using the titles of prince and princess, teaching swimming, providing supplementary explanations for immediate denial, speaking in child-centered language, taking on the supervisory role, starting conversations with specific issues, actively responding to active contact, and going on a trip.

* * * * *